United States Patent
Slezic et al.

(10) Patent No.: US 12,362,050 B2
(45) Date of Patent: *Jul. 15, 2025

(54) SYSTEMS AND METHODS FOR TRANSFERRING MEDICAL DATA FROM MEDICAL DEVICES TO A REMOTE SERVER

(71) Applicant: Stryker Corporation, Kalamazoo, MI (US)

(72) Inventors: Stephen Slezic, Vancouver (CA); Yiu Lun Chu, Richmond (CA); Jessie Ying Chi Ng, Vancouver (CA); Sandeep Kumar Thakur, Miramar, FL (US)

(73) Assignee: Stryker Corporation, Portage, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 18/655,709

(22) Filed: May 6, 2024

(65) Prior Publication Data
US 2025/0006326 A1    Jan. 2, 2025

Related U.S. Application Data

(63) Continuation of application No. 17/184,410, filed on Feb. 24, 2021, now Pat. No. 11,978,544.
(Continued)

(51) Int. Cl.
*G06F 16/535*    (2019.01)
*G06F 3/048*    (2013.01)
(Continued)

(52) U.S. Cl.
CPC ............ *G16H 15/00* (2018.01); *G06F 3/048* (2013.01); *G06F 21/6245* (2013.01); *G16H 40/67* (2018.01)

(58) Field of Classification Search
None
See application file for complete search history.

(56) References Cited

U.S. PATENT DOCUMENTS 6,526,434 B1 *   2/2003   Carlson .................... H04L 9/40
                                                    709/200
2001/0050610 A1  12/2001  Gelston
(Continued)

OTHER PUBLICATIONS

International Preliminary Report on Patentability dated Aug. 30, 2022, directed to International Application No. PCT/US2021/019587; 9 pages.
(Continued)

*Primary Examiner* — Thu N Nguyen
(74) *Attorney, Agent, or Firm* — Morrison & Foerster LLP

(57) ABSTRACT

A method for transferring medical data from a medical device to a remote server includes, at the medical device, tracking a transfer status of medical data stored on a local storage. The stored medical data includes first medical data having a first status and second medical data having a second status. The medical device is physically coupled to a removable data storage device including one or more metadata files. The medical device determines what data is to be transferred to the removable data storage device based on the one or more metadata files and initiates a data transfer process to transfer at least a portion of the first medical data to the removable data storage device based on information determined from reading the one or more metadata files. After completing the data transfer process, the medical device updates the transfer status of the portion of the first medical data.

59 Claims, 6 Drawing Sheets

Related U.S. Application Data

(60) Provisional application No. 62/981,438, filed on Feb. 25, 2020.

(51) Int. Cl.
   *G06F 21/62* (2013.01)
   *G16H 15/00* (2018.01)
   *G16H 40/67* (2018.01)

(56) References Cited

U.S. PATENT DOCUMENTS

| | | |
|---|---|---|
| 2007/0266208 A1 | 11/2007 | Kim et al. |
| 2008/0005121 A1 | 1/2008 | Lam et al. |
| 2008/0133269 A1 | 6/2008 | Ching |
| 2009/0193524 A1 | 7/2009 | Shoji et al. |
| 2010/0293374 A1 | 11/2010 | Bushby |
| 2016/0117813 A1 | 4/2016 | Gross et al. |
| 2016/0135736 A1 | 5/2016 | Bowers |
| 2016/0197885 A1* | 7/2016 | Cismas .................. H04L 67/06 726/26 |
| 2018/0007119 A1* | 1/2018 | Das ...................... H04L 67/568 |

OTHER PUBLICATIONS

International Search Report and Written Opinion mailed Jun. 7, 2021, directed to International Application No. PCT/US2021/019587; 15 pages.

Slezic et al., U.S. Notice of Allowance and Fee(s) Due mailed Dec. 22, 2023, directed to U.S. Appl. No. 17/184,410; 8 pages.

Slezic et al., U.S. Office Action dated Aug. 28, 2023, directed to U.S. Appl. No. 17/184,410; 5 pages.

\* cited by examiner

SYSTEMS AND METHODS FOR TRANSFERRING MEDICAL DATA FROM MEDICAL DEVICES TO A REMOTE SERVER

CROSS-REFERENCE TO RELATED APPLICATIONS

This application is a continuation of U.S. patent application Ser. No. 17/184,410, filed Feb. 24, 2021, which claims the benefit of U.S. Provisional Application No. 62/981,438, filed Feb. 25, 2020, the contents of each of which is incorporated herein by reference in its entirety.

FIELD

The present disclosure relates generally to transferring medical data from a medical device to a remote server and in particular using a removable data storage device to transfer the medical data.

BACKGROUND

Medical devices can be used at healthcare facilities to gather and/or store patient data such as patient vitals data, medical procedure data, recorded videos of a medical procedure, images of a patient's health condition, patient case information, etc. Such healthcare facilities may include, for example, hospitals, clinics, medical centers, doctor's offices, surgical or outpatient centers, etc. Examples of the medical devices may include an operating room (OR) hub, diagnostic equipment such as medical imaging machines (e.g., x-ray machines, MRI machines, PET and CT scanners, etc.), treatment equipment such as infusion pumps, medical monitors, or medical laboratory equipment (e.g., devices to analyze blood, urine, genes, etc.).

For various reasons, many medical devices cannot be connected to the Internet. In some cases, a medical device may not include a network interface and therefore cannot connect to any networks. In other cases, a medical device may be restricted to a local area network at the healthcare facility in which it is used to strengthen the healthcare facility's security posture. In each case, medical data stored locally on the medical devices cannot be easily transferred to a remote server (e.g., a data repository server) for long-term storage.

SUMMARY

As discussed above, medical data stored locally on the medical device may need to be offloaded to a remote server for long-term storage. Accordingly, there exists a need for systems and methods to transfer medical data from a medical device to the remote server. In some embodiments, a removable data storage device (e.g., a USB flash drive or a portable external hard drive) can be physically connected to the medical device to receive and temporarily store the medical device's medical data. Subsequently, the removable data storage device can be connected to a network accessible by the remote server to transfer the stored medical data from the removable data storage device to the remote server.

Simply transferring medical data from the medical device to the removable data storage device for subsequent data offload to the remote server, however, is insufficient and inefficient for at least the following three reasons. First, the medical data often includes patient health information (PHI), which needs to be protected while in transit for patient privacy. Second, transfer statuses of medical data at the medical device need to be managed to prevent redundantly transferring medical data and to prevent limited local storage from quickly filling up. Since the operations of the medical device are disconnected from the remote server, a user may need to manually manage transfer statuses of the stored medical data. For example, the user may need to be aware of operations at both devices to determine which portions of medical data were successfully received and ingested at the remote server as well as which portions of medical data were not successfully ingested and need to be retransferred from the medical device. Third, enabling the user to properly manage the stored medical data at the medical device would require a complex user interface. For example, the user interface would need to enable the user to manually select which data needs to be transferred from the medical device to the removable data storage device as well as allow the user to purge successfully ingested medical data from the medical device to free up storage space on the medical device for storing new medical data. Not only would the user need to be trained as to proper operation of the user interface, but also the complex user interface may induce the user to make mistakes.

Therefore, there exists a further need for systems and methods to securely and efficiently transfer medical data from the medical device to the remote server while improving usability. In some embodiments, such a method can include: at a medical device comprising a local storage: tracking a transfer status of medical data stored on the local storage, wherein the stored medical data comprises: first medical data having a first status indicating that the first medical data is to be transferred from the local storage on the medical device to the remote server but has not been transferred, and second medical data having a second status indicating that the second medical data was previously transferred out of the medical device; physically coupling the medical device to a removable data storage device including one or more metadata files describing contents stored on the removable data storage device; determining what data is to be transferred from the medical device to the removable data storage device based on the one or more metadata files; initiating a data transfer process to transfer at least a portion of the first medical data to the removable data storage device based on information determined from reading the one or more metadata files; and after completing the data transfer process, updating the transfer status of the portion of the first medical data to the second status.

Using this method, the medical device itself can determine what data to transfer based on information that it obtains from the removable data storage device without requiring the user's selection of data. For example, the medical device may identify a command file using the one or more metadata files and obtain commands from the command file that instructs the medical device on which portions of the stored medical data to be transferred or retransferred to the removable data storage device. By configuring the medical device to automatically determine which portions of the stored medical data should be transferred, less medical data may need to be transferred to the removable data storage device. Therefore, the disclosed method can achieve a reduced data transfer time and require less storage space.

Additionally, the medical device maintains transfer statuses for medical data, which allows the medical device to determine which portions of medical data can be safely purged from the local storage. The use of the command file and the transfer statuses may simplify a user interface needed to initiate and operate the medical device and the removable data storage device. In some embodiments, the user interface may present the user with a graphical element to initiate the data transfer process. Upon receiving the user's selection of this graphical element, the medical device can automatically determine which portions of the medical data should be transferred to the removable data storage device and appropriately mark the transfer statuses of portions of the stored medical data. Therefore, the user's operations can be simplified and minimized.

In some embodiments, the stored medical data is obtained in association with a patient, the stored medical data comprising one or more of a sensor reading of a vital sign of the patient, an image of a portion of the patient, a video of a medical procedure of the patient, demographic information of the patient, or information entered by a medical practitioner.

In some embodiments, the medical device is configured to be operated in a hospital and configured to be disconnected from all networks external to the hospital.

In some embodiments, the method includes receiving third medical data at the medical device; determining that the third medical data is prohibited from being transferred out of the medical device; and storing the third medical data to the local storage without associating any transfer statuses with the stored third medical data. In some embodiments, the third medical data comprises personally identifiable information (PII).

In some embodiments, the method includes determining an available storage space on the removable data storage device based on reading the one or more metadata files, wherein the portion of the first medical data is transferred to the removable data storage device based on the determined available storage space.

In some embodiments, the method includes determining whether the removable data storage device has a command file for controlling what data the medical device is to transfer based on reading the one or more metadata files; and the data transfer process is initiated to transfer the portion of the first medical data to the removable data storage device in response to determining that the removable data storage device does not have the command file.

In some embodiments, the method includes identifying a command file stored on the removable data storage device based on reading the one or more metadata files, wherein the command file includes information that controls what data is to be transferred from the medical device to the removable data storage device; and the data transfer process is initiated to transfer the portion of the first medical data to the removable data storage device based on the information in the command file.

In some embodiments, the information in the command file comprises a command to transfer any data having the first status from the medical device to the removable data storage device.

In some embodiments, the information in the command file comprises a command to retransfer previously-transferred data from the medical device to the removable data storage device, and the data transfer process comprises: transferring the second medical data having the second status to the removable data storage device based on the command to retransfer previously-transferred data.

In some embodiments, the information in the command file comprises one or more commands that specify one or more transfer IDs whose corresponding data is to be transferred from the medical device to the removable data storage device, and the data transfer process comprises: identifying one or more portions of the second medical data corresponding to the one or more transfer IDs in the one or more commands; and transferring the one or more identified portions of the second medical data to the removable data storage device.

In some embodiments, the information in the command file indicates which portions of the second medical data were successfully ingested by the remote server.

In some embodiments, the information in the command file comprises second transfer IDs corresponding to the portions of the second medical data.

In some embodiments, the method includes assigning a third status to the portions of the second medical data indicated in the information in the command file, wherein any medical data assigned the third status indicates that the medical data has been successfully ingested by the remote server and is to be purged from the medical device.

In some embodiments, the stored medical data comprises a plurality of data packages assigned a plurality of corresponding transfer identifiers (IDs).

In some embodiments, a first transfer ID for a first data package comprises information indicating a patient, an encounter with the patient that generated the data package, or a data sequence, wherein the information indicating the patient enables the remote server to associate other data packages having the same information indicating the patient with the first data package.

In some embodiments, the portion of the first medical data comprises a plurality of data packages associated with a plurality of transfer IDs, and initiating the data transfer process comprises: retrieving the transfer IDs to generate a list of the plurality of data packages to be transferred based on reading the one or more metadata files; creating a first transfer package for a first transfer ID of the retrieved transfer IDs, wherein the first transfer package comprises first data packages associated with the first transfer ID; and encrypting the first transfer package before transferring the encrypted first transfer package to the removable data storage device.

In some embodiments, creating the transfer package comprises: identifying first source file paths for the first data packages based on the first transfer ID; and combining data from the first data packages based on the identified first source file paths to create an archive file.

In some embodiments, updating the transfer status of the portion of the first medical data comprises: adding to a transfer log one or more entries comprising information that assigns the portion of the first user data with the second status.

In some embodiments, the medical data stored on the local storage comprises medical data generated in response to a user interacting with the medical device.

In some embodiments, the method includes determining which portions of the generated medical data are to be transferred to the remote server based on data types or data sources of the respective portions; and updating a transfer log to indicate that the portions of the generated medical data determined to be transferred have the first status.

In some embodiments, the method includes providing a graphical user interface (GUI) to enable the user to interact with the medical device; and determining whether a portion of the generated medical data is to be transferred based on how the user interacts with the GUI.

In some embodiments, the GUI provides a plurality of graphical elements, and wherein whether the portion of the generated medical data is to be transferred is determined based on which graphical element the user interacted with to generate the portion.

In some embodiments, the method includes updating a data-tracking file during the data transfer process, the data-tracking file comprising information that specifies what data was successfully transferred from the medical device to the removable data storage device; and after completing the data transfer process, transmitting the updated data-tracking file to the removable data storage device.

In some embodiments, the method includes transmitting a copy of the data-tracking file to the removable data storage device before initiating the data transfer process.

In some embodiments, the method includes presenting to a user operating the removable data storage device a user interface that requests the user to enter a user credential; and in response to authenticating the user credential, presenting a graphical element on a screen of the medical device to enable the user to initiate the data transfer process, wherein the data transfer process is initiated in response to receiving the user's selection of the graphical element.

In some embodiments, a system for transferring medical data from a medical device to a remote server, comprises: one or more processors; memory comprising a local storage; and one or more programs, wherein the one or more programs are stored in the memory and configured to be executed by the one or more processors, the one or more programs including instructions for: tracking a transfer status of medical data stored on the local storage, wherein the stored medical data comprises: first medical data having a first status indicating that the first medical data is to be transferred from the local storage on the medical device to the remote server but has not been transferred, and second medical data having a second status indicating that the second medical data was previously transferred out of the medical device; physically coupling the medical device to a removable data storage device including one or more metadata files that describe contents stored on the removable data storage device; determining what data is to be transferred from the medical device to the removable data storage device based on the one or more metadata files; initiating a data transfer process to transfer at least a portion of the first medical data to the removable data storage device based on information determined from reading the one or more metadata files; and after completing the data transfer process, updating the transfer status of the portion of the first medical data to the second status.

In some embodiments, a non-transitory computer-readable storage medium comprises one or more programs for transferring medical data from a medical device to a remote server, wherein the one or more programs, when executed by one or more processors, cause the one or more processors to perform operations comprising: tracking a transfer status of medical data stored on the local storage, wherein the stored medical data comprises: first medical data having a first status indicating that the first medical data is to be transferred from the local storage on the medical device to the remote server but has not been transferred, and second medical data having a second status indicating that the second medical data was previously transferred out of the medical device; physically coupling the medical device to a removable data storage device including one or more metadata files that describe contents stored on the removable data storage device; determining what data is to be transferred from the medical device to the removable data storage device based on the one or more metadata files; initiating a data transfer process to transfer at least a portion of the first medical data to the removable data storage device based on information determined from reading the one or more metadata files; and after completing the data transfer process, updating the transfer status of the portion of the first medical data to the second status.

BRIEF DESCRIPTION OF THE FIGURES

The present disclosure will now be described, by way of example only, with reference to the accompanying drawings, in which.

DETAILED DESCRIPTION

Figure 1:
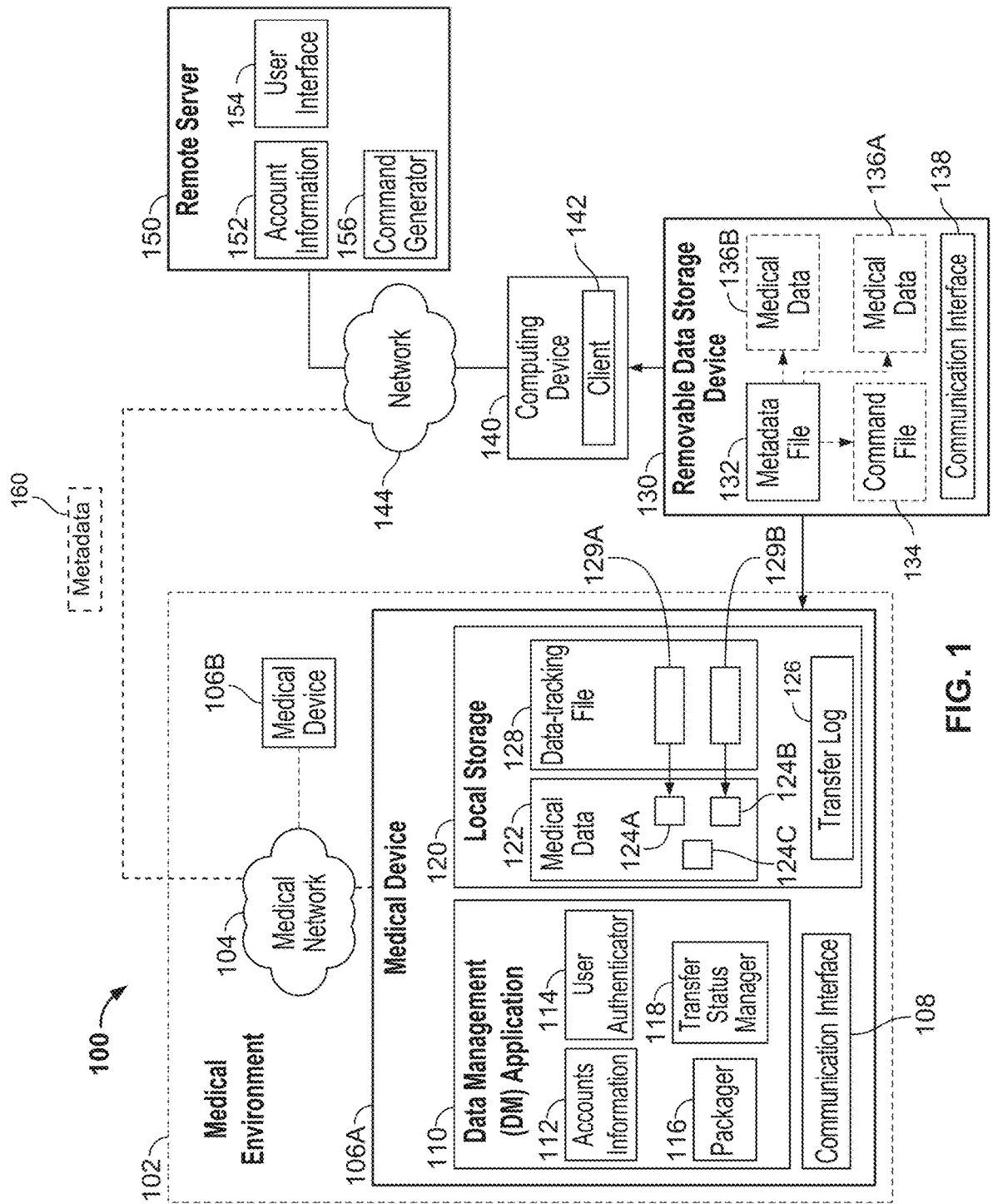
FIG. 1 illustrates a block diagram of a system for transferring medical data from medical devices to a remote server, according to some embodiments.

As discussed above, for security reasons, medical devices are often offline with respect to a remote server and are prevented from directly communicating with the remote server through a network interface to offload medical data. Simply transferring the medical data from the medical device to a portable, temporary storage such as a removable data storage device, from which the temporarily stored medical data can be ported to the remote server is insufficient and cumbersome. Therefore, there exists a need for users to use a removable data storage device to efficiently and securely transfer medical data from the medical device to the remote server.

In some embodiments, the medical device can track transfer statuses of medical data stored on a local storage of the medical device. A transfer status assigned to a data portion may inform the medical device of whether the data portion needs to be transferred, has been transferred, or has been successfully ingested at the remote server. The use of transfer statuses may reduce the burden on users and provide a more robust and efficient data transfer process. Additionally, the medical device can use information, e.g., one or more metadata files, stored on the removable data storage device in conjunction with the tracked transfer statuses to determine which portions of the stored medical data should be transferred to a physically coupled removable data storage device, as will be further described below. For example, the information may include commands read from a command file identified using the one or more metadata files. Such an implementation for the medical device could further increase usability by minimizing operator actions because users would not be required to manually select portions of the stored medical data to be transferred.

In some embodiments, the information in the command file may specify portions of the medical data that were previously transferred out of the medical device and successfully received and ingested at the remote server. The medical device can use this information to determine which portions of the stored medical data can be purged to increase available memory space for storing new medical data. Therefore, the command file in concert with the transfer statuses tracked by the medical device may allow for automated confirmation and processing of successfully transferred medical data, as will be further described below.

In some embodiments, the medical device may provide metadata identifying medical data that is stored on the medical device to a remote computing system, such as via a communication network. The remote computing system may determine from the metadata what medical data that is stored on the medical device should be uploaded to storage. The remote computing system may generate a command file that identifies the medical data that should be uploaded. The command file is then provided to the medical device, such as via transmission from the remote computing system to the medical device over the communication network or via a removable data storage device. The medical device may parse the command file to determine what medical data stored on the medical device should be transferred and may transfer the medical data to the removable data storage device for later uploading to the remote computing system.

In the following description of the various embodiments, reference is made to the accompanying drawings, in which are shown, by way of illustration, specific embodiments that can be practiced. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

As used herein, the singular forms "a," "an," and "the" used in the following description are intended to include the plural forms as well unless the context clearly indicates otherwise. It is to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present invention include process steps and instructions described herein in the form of a method. It should be noted that the process steps and instructions of the present invention could be embodied in software, firmware, or hardware, and, when embodied in software, they could be downloaded to reside on, and be operated from, different platforms used by a variety of operating systems. Unless specifically stated otherwise as apparent from the following discussion, it is appreciated that, throughout the description, discussions utilizing terms such as "processing," "computing," "calculating," "determining," "displaying," or the like refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates a block diagram of a system 100 for transferring medical data from medical devices 106A-B to a remote server 150, according to some embodiments. System 100 includes medical devices 106A-B in a medical environment 102 that may be separate and disconnected from remote server 150 and network 144 accessible by remote server 150, according to some embodiments. Medical environment 102 may refer to an operating room environment or within, for example, a hospital or other healthcare facility. In some embodiments, medical devices 106A-B may include, for example, an operating room hub, diagnostic equipment, treatment equipment, medical monitors, or medical laboratory equipment. In some embodiments, medical devices 106A-B such as medical device 106B may include storage hardware for storing medical data. For example, such storage hardware may include a file server, a Picture Archiving and Communication System (PACS) server, an Electronic Medical Record (EMR) server, etc. As shown in FIG. 1, the storage hardware such as medical device 106B may be connected to medical network 104 and restricted to medical environment 102.

Some medical devices such as medical device 106B may be capable of accessing a medical network 104 via, for example, a wired Ethernet connection. Medical network 104 may include one or more private networks such as a Local Area Network (LAN) or a Wide Area Network (WAN) that enables devices within medical environment 102 to communicate with each other. Other medical devices such as medical device 106A may not be capable of accessing any networks including medical network 104. For example, medical device 106A may not include a network interface such as a network interface card (NIC) or a wireless network interface controller (WNIC). In each case, medical devices 106A-B may be configured to be offline devices with respect to remote server 150 and cannot connect to a communication network such as network 144 accessible by remote server 150.

In the medical context, restricting medical devices 106A-B from accessing computer networks, such as network 144, outside medical environment 102 increases the security posture at healthcare facilities and better protects the medical data of patients. For similar reasons, medical network 104 may be configured to be inaccessible to devices, such as remote server 150, outside of medical environment 102. As will be further described below, to enable data transfer between network-disconnected devices, medical devices 106A-B and remote server 150 can be configured to interface with removable data storage device 130 (e.g., a portable USB drive) that serves as intermediary storage to port medical data stored on medical devices 106A-B to remote server 150 for long term storage, according to some embodiments.

In some embodiments, a medical device, such as medical device 106A is capable of accessing one or more networks, including medical network 104 and network 144, such as to communicate with remove server 150. In some embodiments, a medical device 106A that can access a communication network may be restricted with respect to the information that the medical device 106A can exchange. For example, a networked medical device 106A may be communicatively connected to remote server 150 but may be restricted from transferring certain types of data, such as medical data, to the remote server over the network connection. Instead, as discussed further below, restricted data, such as medical data, may be transferred via the removable data storage device 130.

In some embodiments, removable data storage device 130 can include a data storage external to medical devices 106A-B. For example, removable data storage device 130 may include a USB flash drive (i.e., a memory stick, a pen drive, a USB drive, etc.), a CD, a DVD, an external hard disk drive, etc. In some embodiments, removable data storage device 130 includes a communication interface 138 that permits removable data storage device 130 to be communicatively coupled to medical devices 106A-B. For example, removable data storage device 130 may include a USB connector that allows a user to insert removable data storage device 130 into, for example, a USB port of medical device 106A to enable data communications through the physical connection.

In some embodiments, removable data storage device 130 can be configured with a file system for storing medical data. In some embodiments, removable data storage device 130 includes one or more metadata files such as metadata file 132 that describe contents stored on removable data storage device 130. In some embodiments, metadata file 132 can include one or more of: a master file table (MFT), an index table, directory information, free space bitmap, block availability map, etc.

In some embodiments, metadata file 132 can include information related to an amount of available storage space on the removable data storage device. For example, metadata file 132 may include information that describe free space or unallocated space (e.g., a free space bitmap or a block availability map) or size of files currently stored on the removable data storage device.

In some embodiments, metadata file 132 can include directory and/or file indexing information that describe what contents are stored on the removable data storage device as well as where such contents are stored. For example, directory information may indicate a presence of one or more files such as command file 134 or one or more medical data 136A-B as well as where the one or more files are stored on removable data storage device 130. In some embodiments, metadata file 132 can include file indexing information that allows a connected device such as medical device 106A to more efficiently determine whether a specific file exists and locate a file determined to exist.

In some embodiments, medical data transferred from a medical device, such as medical device 106A, can be stored as medical data 136A-B. As data portions 124A-B of medical data 122 is transferred from local storage 120 of medical device 106A for storage as medical data 136A-B, removable data storage device 130 can be configured to update metadata file 132 to indicate stored medical data 136A-B. For example, metadata file 132 may be updated to indicate an amount of storage space allocated to and used by stored medical data 136A-B. In another example, metadata file 132 may be updated to specify where medical data 136A-B are stored on removable data storage device 130.

In some embodiments, removable data storage device 130 can store a command file 134 that includes information for controlling what data is to be transferred from the connected device such as medical device 106A to removable data storage device 130. For example, command file 134 may include one or more commands that specify a type of medical data to transfer such as medical data having a specified transfer status. In another example, the one or more commands in command file 134 may list one or more transfer IDs whose associated medical data is to be transferred. Further embodiments and examples of command file 134 are described below with respect to FIGS. 3-5.

In some embodiments, command file 134 can include device information that specify a particular medical device such as medical device 106A. By including the device information, removable data storage device 130 may be configured to operate with only the medical device indicated by the device information, according to some embodiments. For example, when removable data storage device 130 is physically coupled to medical device 106A, medical device 106A may check the device information in command file 134 to determine whether medical device 106A is permitted to transfer stored medical data to removable data storage device 130.

In some embodiments, a medical device, such as medical device 106A may have the ability to communicate with the remote server 150 over the network 144 and medical network 104 and may communicate information to the remote server 150 that the remote server 150 uses to generate the command file 134. For example, medical device 106A may transmit information regarding the medical data 122 stored on the medical device 106A to the remote server 150, and the remote server 150 may generate or update the command file 134 based on the information received from the medical device 106A. In some embodiments, the remote server 150 may send a request to the medical device 106A for information indicating the contents of medical data 122 stored on the medical device 106A. In response to the request from the remote server 150, the medical device 106A may transmit metadata 160 to the remote server that provides identifying information for the contents of the medical data 122. The remote server 150 may use the information in the metadata 160 to determine medical data stored on the medical device 106A that should be transferred from the medical device 106A. The remote server 150 may then generate or update the command file 134 to include information identifying which medical data should be transferred via the removable data storage device 130.

In some embodiments, the request for the metadata 160 may include criteria defining the scope of the request. For example, the remote server 150 may request all new medical data files created or modified in a certain time period (e.g., the previous day, within the past week, from date X to date Y, etc.) or may request all medical data files of a particular type. In response to the request, the medical device 106A may generate the metadata file 160 to include information related to each portion of medical data 122 that meets the criteria of the request. For example, the information may include a filename, a file size, a creation date, a file type, and/or any other metadata for each medical data file meeting the criteria of the request. The remote server 150 may use this information to identify in the command file 134 the medical data that should be transferred to the removable data storage device 130 in the next transfer.

In some embodiments, the medical device 106A may have the ability to transfer medical data 122 to the remote server 150 over a network connection (e.g., via medical network 104 and network 144), and sending the command file 134 to the medical device 106A and receiving the medical data 122 from the medical device 106A may occur over the network connection. In some embodiments, the medical device 106A may be permitted to transfer metadata 160 to the remote server 150 over the network connection but may be restricted from transferring the medical data 122 to the remote server 150 over the network connection, such to increase data security. Thus, in some embodiments, the metadata 160 may be transmitted from the medical device 106A to the remote server 150 over the network connection but the command file 134 is provided on the removable data storage device 130 and the medical data 122 is transferred via the removable data storage device 130.

In some embodiments, to enable data communications with removable data storage device 130, each of medical devices 106A-B such as medical device 106A can include a communication interface 108, data management (DM) application 110, and a local storage 120. In some embodiments, communication interface 108 includes one or more ports that support one or more respective data communication protocols to enable data transfer between medical device 106A and removable data storage device 130 when removable data storage device 130 is physically coupled to medical device 106A. For example, removable data storage device 130 may include a USB connector that plugs into a USB port of medical device 106A to communicatively couple medical device 106A to removable data storage device 130. Examples of the one or more data communication protocols may include any of the following: Thunderbolt, USB 3.1, USB 3.0, eSATA, Firewire, Gigabit Ethernet, USB 2.0, or Ethernet.

In some embodiments, local storage 120 includes one or more data storage devices for storing medical data 122 at medical device 106A. For example, local storage 120 may include one or more non-volatile storage (i.e., also referred to as non-volatile memory (NVM)) such as flash memory (e.g., a solid state drive) or a hard disk drive. As shown in system 100, stored medical data 122 may include data portions 124A-C. In some embodiments, each of data portions 124A-C may include a plurality of data packages generated at or received by medical device 106A, as will be further described below with respect to FIG. 2.

Medical data 122 are generated for or based on patients and can include different types of data. In some embodiments, medical data 122 can include data gathered by medical equipment. For example, data portion 124A of medical data 122 may include patient vitals data sensed by a vitals monitor, images of a patient's body taken by medical imagining machines such as an MRI machine or an x-ray machine, or videos taken by a camera or an endoscope of a surgical procedure, etc. In another example, data portion 124B may include data sensed by treatment equipment such as blood readings, urine analysis, gene analysis, etc. In some embodiments, medical data 122 can include medical data entered by hospital personnel. For example, data portion 124C may include patient details such as a full legal name and address entered by a hospital receptionist for a patient. In another example, data portion 124A may include, for example, surgical procedure information or patient encounter or case information entered by a doctor or a surgeon for the patient.

In some embodiments, local storage 120 stores a data-tracking file 128 that tracks transfer statuses 129A-B of one or more data portions 124A-B of stored medical data 122. For example, transfer statuses 129A and 129B may be assigned to data portions 124A and 124B, respectively. In some embodiments, as will be further described below with respect to FIG. 2, a transfer status for an associated data portion may track whether that data portion should be transferred out of local storage 120 for long-term storage, whether that data portion was transferred out of local storage 120 to removable data storage device 130, and whether that data portion was successfully received and ingested at remote server 150. In some embodiments, certain portions of medical data 122 such as data portion 124C may not have an assigned transfer status in data-tracking file 128 because medical device 106A determined that data portion 124C should not be transferred out of local storage 120. For example, data portion 124C may include personally identifiable information (PII) and therefore should not be transferred. In another example, data portion 124C may include derived data that can be recreated based on one or more other data portions 124A-B. For example, for medical data 122 related to clinical trials, data portion 124C may be created to permit generation of analysis results or speed up data analysis. Whereas the analysis results are relevant to the clinical trials and should be transferred for external backup, the intermediary data in data portion 124C may not be relevant and does not need to be backed up.

In some embodiments, local storage 120 can include a transfer log 126 that records operations between medical device 106A and a physically-coupled removable data storage device such as removable data storage device 130. In some embodiments, these operations may include which files were transferred from local storage 120 and when such files were transferred. For example, transfer log 126 may include one or more entries that specify which portions of medical data 122 were successfully transferred to removable data storage device 130. In another example, during a data transfer process, when a data portion is transferred, transfer log 126 may be updated to reflect whether the data portion was successfully transferred. Other example operations that may be logged in transfer log 126 include, without limitation, when the transfer process starts, whether data-tracking file 128 was transferred, which of data portions 124A-B were transferred, statuses of transferred data portions 124A-B, etc. In other embodiments, transfer log 126 may also record user operations of medical device 106A. For example, such logged information may include which user initiated a data transfer, which options were selected by the user, and when such user operations were detected, etc.

In some embodiments, DM application 110 can be configured to manage how and whether medical data 122 is to be transferred from local storage 120 to removable data storage device 130 as well as track transfer statuses for corresponding data portions of stored medical data 122. To provide these functionalities, DM application 110 can include the following components: user authenticator 114, packager 116, and transfer status manager 118. In some embodiments, each of these components may include a set of programming instructions that when executed by a processor of medical device 106A causes the medical device 106A to perform the functionality of the component.

In some embodiments, medical device 106A can provide a user interface that enables a user to operate medical device 106A. The user interface can request the user to enter his or her user credentials before permitting the user to transfer any medical data out of local storage 120. For example, the user interface may prompt the user with a login screen that requests the user to enter user credentials such as a username and a password. In some embodiments, user authenticator 114 can be configured to compare the received user credentials against stored accounts information 112 to determine whether the user is permitted to transfer data portions 124A-B of medical data 122 out of local storage 120. For example, accounts information 112 may include a plurality of permitted user accounts. Each permitted user account may include a username and an associated password.

In some embodiments, if the user is authenticated by user authenticator 114, the user interface can be configured to display a graphical element that when selected by the user initiates a data transfer process. In some embodiments, the user interface may request the user to physically couple (e.g., insert) removable data storage device 130 to medical device 106A if no connected removable data storage devices are connected. As discussed above and will be further described below, because medical device 106A manages transfer statuses of portions 124A-B of stored medical data 122, medical device 106A can automatically determine which portions of medical data 122 should be transferred without user input. Therefore, the user interface does not need to request the user to select which portions of medical data 122 should be transferred to removable data storage device 130. Additionally, certain portions of medical data such as data portion 124C that include PII should not be transferred and can be better protected because the user cannot control which portions of medical data are to be transferred.

In some embodiments, transfer status manager 118 can be configured to determine which data portions to transfer from medical data 122 to removable data storage device 130 based on data-tracking file 128 and information obtained from removable data storage device 130. For example, as will be further described below with respect to FIG. 3, transfer status manager 118 may identify a presence of command file 134 stored on a physically coupled removable data storage device 130 by reading metadata file 132.

In some embodiments, transfer status manager 118 can be configured to obtain one or more commands from a retrieved command file 134. The one or more commands may specify which portions of medical data 122 to be transferred. For example, a command may indicate that data packages associated with specific transfer IDs should be transferred. In another example, a command may indicate that any data portions having a transfer status of pending transfer (i.e., to-be-transferred) should be transferred to removable data storage device 130. Therefore, transfer status manager 118 can use data-tracking file 128 and the information from command file 134, if present, to identify one or more transfer IDs in data-tracking file 128 whose associated data portions are to be transferred, according to some embodiments.

In some embodiments, transfer status manager 118 can be configured to update transfer statuses of data portions in data-tracking file 128. For example, if data portion 124A was transferred to removable data storage device 130, transfer status manager 118 may update transfer status 129A of data portion 124A to a transfer status indicating the transfer. In another example, command file 134 may indicate previously-transferred data portions that were successfully ingested by remote server 150. In this example, transfer status manager 118 may update transfer statuses corresponding to these previously-transferred data portions to a transfer status indicating the successful ingestion, as will be further described below with respect to FIGS. 2-3. In some embodiments, DM application 110 can be configured to purge or overwrite these marked previously-transferred data portions from local storage 120 because they have been successfully stored on remote server 150.

In some embodiments, data-tracking file 128 can be implemented as an XML file to track the data portions (e.g., data packages) and associated transfer statuses. In some embodiments, transfer status manager 118 can be configured to transfer: a first copy of data-tracking file 128 to removable data storage device 130 before a data transfer process, and a second copy of data-tracking file 128 at the end of a data transfer process. These copies of data-tracking file 126 may provide data transfer information that permits remote server 150 to determine which data portions were successfully transferred as well as which data portions may need to be retransferred.

In some embodiments, transfer status manager 118 can be configured to track transfer operations between medical device 106A and removable data storage device 130 in transfer log 126. For example, after transferring a data portion to removable data storage device 130, transfer status manager 118 may not only update the transfer status of that data portion, but also transfer status manager 118 may add an entry to transfer log 126 indicating the transfer. In some embodiments, transfer status manager 118 can be configured to transfer a copy of transfer log 126 to removable data storage device 130 at the end of a data transfer process. This transfer log 126 may provide a historical record for operations of medical device 106A to prevent unnecessary retransfer of medical data as well as to record user operations on medical device 106A. In some embodiments, once the data transfer process completes, the user interface may display a notification to the user. Then, the user may disconnect removable data storage device 130 from medical device 106A.

In some embodiments, packager 116 can be configured to generate a transfer package to transfer a data portion of medical data 122 to removable data storage device 130. As described above, transfer status manager 118 may identify one or more transfer IDs whose associated data packages are to be transferred. In some embodiments, for each identified transfer ID, packager 116 may retrieve a plurality of data packages associated with that transfer ID. Then, packager 116 may combine the plurality of data packages into an archive file. For example, packager 116 may compress data packages to generate a ZIP file. To generate the transfer package, packager 116 may be configured to encrypt the archive file using an encryption algorithm such as Advanced Encryption Standard (AES). A skilled person would understand that other types of compression formats and encryption algorithms can be used. Further embodiments for generating the transfer package are described below with respect to FIG. 4.

Returning to removable data storage device 130, once the data transfer process completes and medical data 136A-B are stored on removable data storage device 130, the user may be prompted to physically disconnect removable data storage device 130 from a connected medical device such as medical device 106A. In some embodiments, to port stored medical data 136A-B from removable data storage device 130 to remote server 150, removable data storage device 130 needs to be physically transported to a computing device 140 capable of accessing remote server 150.

In some embodiments, computing device 140 can be a device capable of connecting to network 144 accessible by remote server 150. For example, computing device 140 may be a laptop, a desktop computer, a tablet, a smartphone, or other networked devices. Network 144 may include the Internet, a wired network, a wireless network, a Local Area Network (LAN), a wide area network (WAN), or a combination thereof. In some embodiments, computing device 140 includes a client 142 such as a browser or client application capable of connecting to remote server 150. For example, client 142 may access a web portal provided by a user interface 154 of remote server 150.

In some embodiments, remote server 150 can include account information 152, user interface 154, and a command generator 156. In some embodiments, account information 152 may include a plurality of user accounts permitted to upload medical data to remote server 150 for long-term storage. Each permitted user account may include a username and an associated password. In some embodiments, the user can access user interface 154 of remote server 150 through client 142. User interface 154 may display a login screen that requests the user to enter his or her user credentials to gain access to remote server 150. User interface 154 can be configured to compare entered user credentials against stored account information 152 to determine whether to permit the user to transfer medical data from removable data storage device 130 to remote server 150.

In some embodiments, once the user has been authenticated, user interface 154 may present a graphical element that when selected initiates a data transfer process. In some embodiments, command generator 156 can be configured to track an ingestion status for each portion of medical data stored on removable data storage device 130. For example, command generator 156 may track which portions of medical data were successfully received and ingested at remote server 150 as well as which portions of medical data were not successfully ingested. In some embodiments, as will be further described below with respect to FIG. 5, command generator 156 can be configured to generate a command file that includes information related to the ingestion status for the plurality of portions of the ingested medical data. Then, command generator 156 may write the generated command file to removable data storage device 130. As described above, the command file includes one or more commands that will control how a medical device is to transfer medical data when removable data storage device 130 is later communicatively coupled to that medical device such as medical device 106A.

In some embodiments, command generator 156 generates a command file, such as command file 134, based on metadata 160 that is received from the medical device 106A via a network connection with the medical device 106A (e.g., network 144 and medical network 104). In some embodiments, the command generator 156 may generate the command file 134 (as used here, the term generate includes updating a previously created command file) based on information received from the medical device 106A via the network. For example, the medical device 106A may transmit metadata indicating one or more medical data files stored on the medical device 106A to the remote server 150 via the medical network and network 144. In some embodiments, the medical device 106A transmits the metadata in response to a request from the remote server 150. The remote server 150 may transmit a request to the medical device 106A to provide metadata associated with the medical data stored on the medical device 106A. In some embodiments, the server 150 may include criteria in its request that may limit what medical data the medical device 106A identifies in its response to the request. The criteria can include date criteria, such as a medical data file creation or modification date range, a medical data file type, a medical data file size, all medical data created or modified since a last update, medical data that has not yet been transferred to a removable data storage device 130, all medical data, or any other suitable criteria. In response to the request, the medical device 106A may transmit to the remote server 150 metadata identifying the medical data stored on the medical device 106A that meets the criteria in the request from the remote server 150. The metadata could include, for example, medical data file names and local directory locations. The remote server 150 may then use this information to specify in the command file 134 which medical data should be transferred to the removable data storage device 130 at the next transfer. Then, command generator 156 may write the generated command file to removable data storage device 130.

In some embodiments, removable data storage device 130 communicatively coupled to remote server 150 may be empty and does not store any medical data 136A-B. In these embodiments, user interface 154 may be configured to allow the user to select one or more medical devices whose medical data are to be ported to remote server 150 using removable data storage device 130. In some embodiments, for each selected medical device, command generator 156 can be configured to generate a corresponding command file including information that controls how that medical is to transfer its medical data. In these embodiments, each command file may store a device identifier that identifies the medical device associated with the command file.

Figure 2:
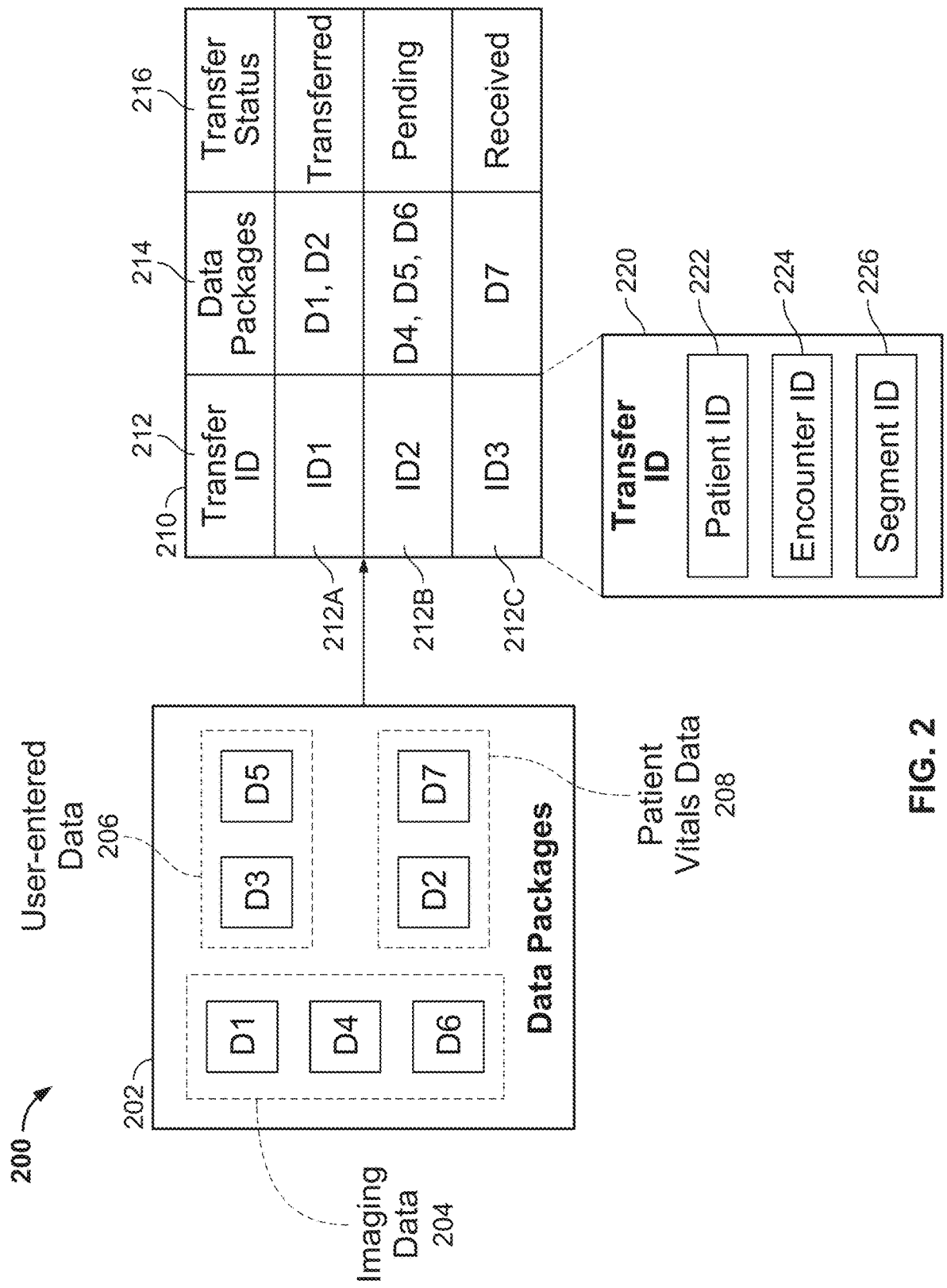
FIG. 2 illustrates an example diagram that shows how a medical device tracks and manages data packages stored on a local storage of the medical device, according to some embodiments.

FIG. 2 illustrates an example diagram 200 that shows how a medical device tracks and manages data packages 202 stored on a local storage of the medical device, according to some embodiments. For example, the medical device may include medical device 106A as described above with respect to FIG. 1.

As shown in diagram 200, the medical device can store received medical data (e.g., medical data 122) as a plurality of data packages 202 labeled as D1-D7. In some embodiments, data packages 202 can be received from a plurality of different sources and include different types of data. For example, data packages 202 may include imaging data 204 (e.g., data packages D1, D4, and D6) received from an imaging device such as an endoscope, an X-ray machine, an MRI machine, etc. As another example, data packages 202 may include patient vitals data 208 (e.g., data packages D2 and D7) received from a vitals monitor. Additionally, data packages 202 may include user-entered data 206 (e.g., data packages D3 and D5) such as data entered by medical personnel including, for example, a doctor, a nurse, or a surgeon. For example, data package D3 may include personally identifiable information (PII) such as a patient's name and data package D5 may include medical operation details and notes entered by the doctor.

In some embodiments, when data packages are received at the medical device, the medical device (e.g., transfer status manager 118 of medical device 106A) can be configured to assign transfer statuses as well as transfer identifiers (IDs) to the data packages in a data-tracking file 210 (e.g., data-tracking file 128). For example, the medical device may be configured to determine whether a received data package should be assigned a 'Pending' transfer status to indicate that the received data package should be transferred to a remote server for long-term storage. For example, the medical device may determine that received data package D3 includes PII and therefore should not be assigned any transfer statuses. Therefore, data-tracking file 210 does not associate data package D3 with any transfer statuses 216 or transfer IDs 212.

In some embodiments, data-tracking file 210 can associate transfer IDs 212 with data packages 214 and transfer statuses 216. In some embodiments, the medical device (e.g., transfer status manager 118 of medical device 106A) can associate one or more related data packages with the same transfer ID. For example, data packages D1 and D2 may be associated with transfer ID 1; data packages D4, D5, and D6 may be associated with transfer ID 2; and data package D7 may be associated with transfer ID 3. In some embodiments, each transfer ID can be associated with one or more data packages by storing one or more links corresponding to the one or more data packages. For example, transfer ID 2 may be associated with three source file paths corresponding to data packages D4, D5, and D6. A source file path may identify where an associated data package is stored on the medical device to permit retrieval of that data package. As shown in diagram 200, data-tracking file 210 may store the associations in a table. Other data structures for storing these associations are possible and well-known by those skilled in the relevant arts.

In some embodiments, transfer ID 220 shows an example of one of transfer IDs 212. As shown in diagram 200, transfer ID 220 may include a patient ID 222 that indicates a particular patient, an encounter ID 224 that identifies a particular visit or session between the patient and a healthcare facility or a doctor, and a segment ID 226 that indicates a specific segment of data. In some embodiments, patient ID 222, encounter ID 224, and segment ID 226 may correspond to portions of transfer ID 220. Therefore, patient ID 222, encounter ID 224, and segment ID 226 may be extracted from transfer ID 220. In some embodiments, transfer ID 220 may be assigned to data packages that were generated for the same patient during a single encounter or session between the patient and a doctor at a healthcare facility. In some embodiments, a data package may include metadata and/or binary files associated with patient ID 222, encounter ID 224, or segment ID 224.

In some embodiments, patient ID 222 can include de-identified information that can be used to correlate data for the same patient, but does not enable identification of the patient based on the de-identified information alone. For example, patient ID 222 may be a sequence of alphanumeric characters that cannot be used to independently derive the corresponding patient's identity. As shown in diagram 200, data packages for transfer IDs 212 that have the same patient ID 222 may include data for the same patient. For example transfer IDs 212A and 212B may have the same patient ID and indicate that data packages D1, D2, D4, D5, and D6 corresponding to transfer IDs 212A-B include data for the same patient. Transfer ID 212C may include a different patient ID 222, which indicates that data package 7 includes data for a different patient.

In some embodiments, encounter ID 224 may enable data packages in different data segments, as identified by segment ID 226, to be correlated to the same patient visit or session. For example, data packages generated for a patient during one encounter may be assigned the same encounter ID 224.

In some embodiments, the medical device can also track transfer statuses 216 for corresponding transfer IDs 212 and data packages 214. For example, when data packages D4, D5, and D6 were received by the medical device, the medical device can assign transfer ID 212B ('ID 2') and a transfer status of 'Pending' to the data packages. When data packages associated with a transfer ID are transferred to a removable data storage device, the medical device can update an associated transfer status. For example, data packages D1 and D2 associated with transfer ID 212A ('ID 1') may have been transferred and therefore assigned a transfer status 216 of 'Transferred.' When the medical device receives indication that previously-transferred data packages were successfully received and ingested by the remote server, the medical device can update an associated transfer status. For example, data package D7 associated with transfer ID 212C ('ID 3') may have been determined to be successfully ingested by the remote server and therefore assigned a transfer status 216 of 'Received.' As will be further described below, the medical device can be configured to purge data portions having a transfer status (e.g., 'Received') that indicates the data portions were successfully ingested at the remote server.

In some embodiments, as will be further described below, the medical device (e.g., packager 116 of medical device 106A) can be configured to use data-tracking file 210 to generate transfer packages for transferring medical data from the medical device to the removable data storage device. For example, the medical device may receive a command from a command file to transfer medical data having a transfer status of 'Pending'. In this example, the medical device may identify transfer ID 212A as having the 'Pending' transfer status. Then, the medical device may generate a transfer package that combines data from data packages D1 and D2 associated with transfer ID 212A. In some embodiments, the medical device can compress and encrypt the transfer package before transferring the data to the removable data storage device.

Figure 3:
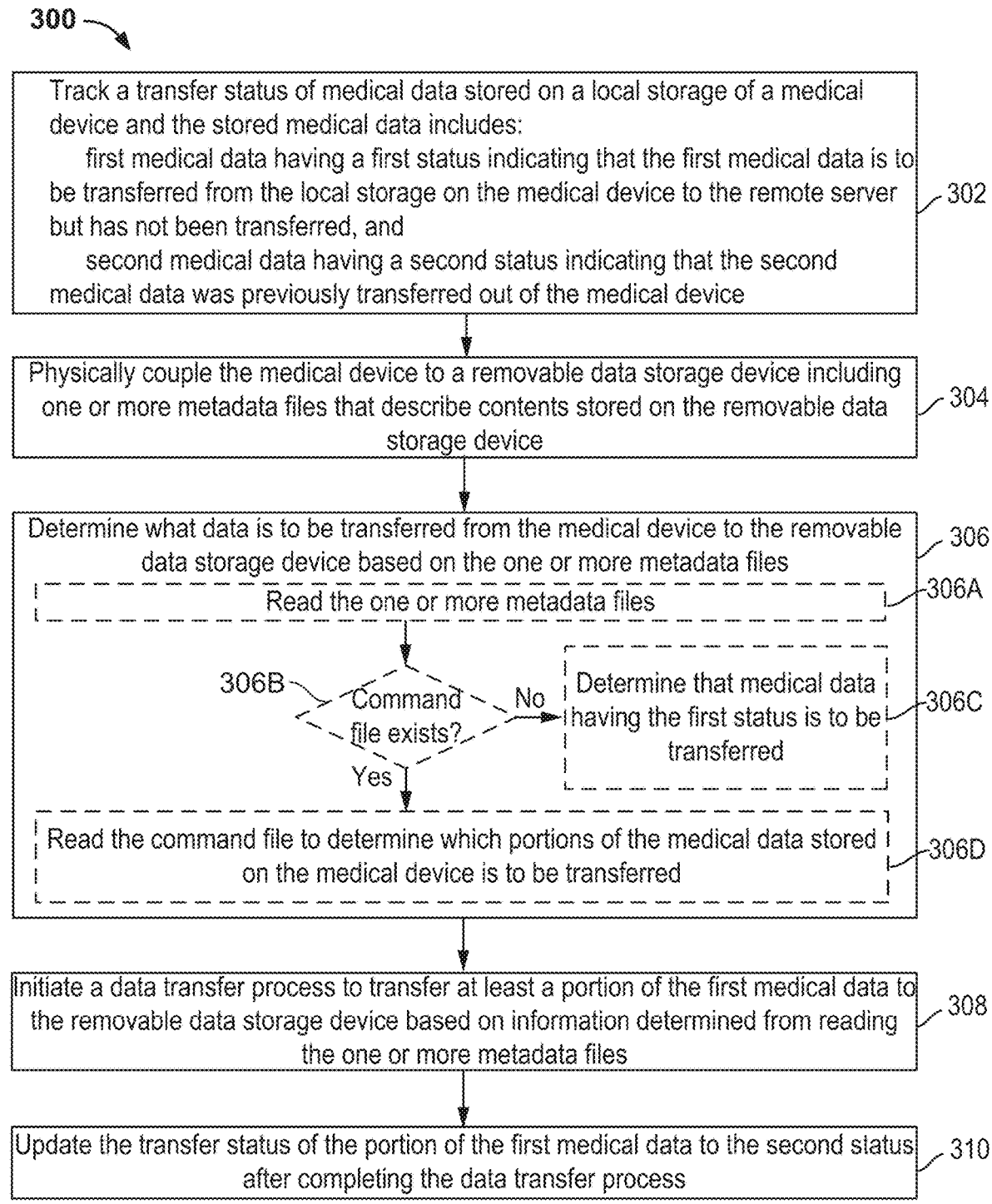
FIG. 3 illustrates a flowchart of a method for transferring data from a medical device to a remote server, according to some embodiments.

FIG. 3 illustrates a flowchart of a method 300 for transferring medical data from a medical device to a remote server, according to some embodiments. Method 300 can be performed by the medical device such as medical device 106A of FIG. 1. As describe above with respect to FIG. 1, the medical device may be configured to be an offline device with respect to the remote server and is not connected to any communication networks accessible by the remote server. For example, the medical device may not include any network interfaces or may be restricted from accessing communication networks external to a medical environment in which the medical device is being used.

In step 302, the medical device tracks a transfer status of medical data stored on a local storage of the medical device and the stored user data includes: first medical data having a first status indicating that the first medical data is to be transferred from the local storage on the medical device to the remote server but has not been transferred, and second medical data having a second status indicating that the second medical data was previously transferred out of the medical device. For example, in the embodiment shown in diagram 200 of FIG. 2, the first medical data may include data packages D4, D5, and D6 associated with a transfer ID 212B having the 'Pending' transfer status corresponding to the first transfer status. In this same example, the second medical data may include data packages D1 and D2 associated with a transfer ID 212A having the 'Transferred' transfer status corresponding to the second transfer status.

In some embodiments, when the medical device receives third medical data (e.g., newly received medical data) to be stored on the local storage, the medical device can be configured to determine whether to assign the third medical device the first status based on a type, a source, a content, or a combination thereof of the new medical data. For example, the medical device may determine that the third medical data includes personally identifiable information (PII) and should not be transferred out of the medical device. In some embodiments, the medical device would therefore store the third medical data to the local storage without assigning it the first status. For example, in the embodiment shown in FIG. 1, medical data 122 includes a data portion 124C that is not assigned any transfer statuses in data-tracking file 128.

In some embodiments, the medical device maintains a data-tracking file (e.g., data-tracking file 128) that stores a plurality of transfer statuses corresponding to a plurality of portions of the stored medical data. As described above, a transfer status assigned to a data portion may include: the first status indicating that the data portion is to be transferred, or the second status indicating that the data portion was previously transferred out of the medical device. In some embodiments, the transfer status for the data portion may include a third status indicating that the data portion was successfully ingested by the remote server and can be purged from the local storage of the medical device. For example, in the embodiment shown in FIG. 2, the third status is shown as 'Received' and indicates the data package D7 corresponding to transfer ID 212C was successfully ingested by the remote server.

In step 304, the medical device physically couples the medical device to a removable data storage device (e.g., removable data storage device 130) including one or more metadata files that describe contents stored on the removable data storage device. For example, the removable data storage device may be a USB flash drive. In some embodiments, the medical device includes a communication interface (e.g., a USB port) that allows a user to insert the removable data storage device into the medical device to communicatively couple the two devices. As described above with respect to FIG. 1, a metadata file (e.g., metadata file 132) may be a storage-system dependent file used to manage storage of data. For example, the metadata file can include directory or file indexing information that describe what contents are stored on the removable data storage device as well as where such contents are stored. The metadata file may also include information related to an amount of available storage space on the removable data storage device.

In step 306, the medical device determines what data is to be transferred from the medical device to the removable data storage device based on the one or more metadata files. In some embodiments, to determine what data is to be transferred, step 306 can include one or more steps 306A-D.

In step 306A, the medical device reads the one or more metadata files to determine whether the removable data storage device includes a command file for controlling what data the medical device is to transfer to the removable data storage device. For example, the medical device may read file directory information or file indexing information from the one or more metadata files to identify a presence of the command file and retrieve information from the command file. For example, the medical device may search the removable data storage device for the command file (e.g., a predefined file name of the command file) using the one or more metadata files.

In some embodiments, the medical device can read the one or more metadata files to aid in transfer of medical data. For example, the medical device may determine an amount of available storage space on the removable data storage device based on information stored in the one or more metadata files.

In step 306B, the medical device determines whether the command file exists based on reading the one or more metadata files in step 306A. If no command file is present, method 300 proceeds to step 306C. Otherwise, method 300 proceeds to step 306D.

In step 306C, the medical device determines that medical data having the first status is to be transferred. In some embodiments, step 306C corresponds to a default operation of the medical device in the absence of any command files. In some embodiments, the default operation of step 306C may correspond to a command to transfer all medical data tagged by the first status as data to be transferred but has not been transferred. In these embodiments, by default, the medical device may be configured to defer retransmitting and/or assigning an updated transfer status to medical data tagged by the second status until a command file may be found during a later transfer session that specifies whether medical data tagged by the second status was successfully ingested by the remote server.

In step 306D, the medical device reads the command file to determine which portions of the medical data stored on the medical device is to be transferred. In some embodiments, the command file includes information that controls what data the medical device is to transfer from the local storage to the removable data storage device. In some embodiments, the medical device can be configured to retransmit a portion of the second medical data that was previously transferred out of the medical device based on the command file. For example, the command file may indicate that a portion of the second medical data was not successfully ingested by the remote server. In some embodiments, the information can include one or more commands. For example, the information may include one or more of: a command to transfer any data having the first status (i.e., transfer new data that was not previously transferred out of the medical device); a command to retransfer data associated with a transfer ID; or a command to transfer all data having the second status (i.e., retransfer previously-transferred medical data).

In step 308, the medical device initiates a data transfer process to transfer at least a portion of the first medical data to the removable data storage device based on information determined from reading the one or more metadata files. In some embodiments, the medical device can be configured to transfer specific data based on whether a command file is identified from reading the one or more metadata files. For example, if no command file is identified, the medical device may transfer any medical data (e.g., the first medical data) having the first status to the removable data storage device, as described in step 306C. In some embodiments, the medical device may transfer as much of the first medical data as possible based on available memory storage on the removable data storage device. Therefore, in some instances, all of the first medical data may be transferred if available memory storage exists.

In some embodiments, the medical device can be configured to transfer a copy of the data-tracking file to the removable data storage device before transferring the portion of the first medical data.

In some embodiments, the medical device is configured to provide a user interface to authenticate the user before initiating the data transfer process. In some embodiments, after authenticating the user, the user interface is configured to present the user with an option to transfer data to the removable data storage device. In these embodiments, the user interface is configured to prevent the user from selecting which portions of the medical data stored on the local storage is to be transferred out of the medical device.

In some embodiments, the command file can include information (e.g., a command) indicating that a previously-transferred data portion was successfully ingested by the remote server. For example, a command in the command file may specify one or more transfer IDs corresponding to one or more portions of the second medical data that were previously transferred out of the medical device. In some embodiments, the medical device can be configured to purge the one or more portions of the second medical data from the local storage of the medical device. In other embodiments, the medical device can be configured to assign the one or more portions of the second medical data with a status (e.g., described as third status with respect to step 302) indicating that the one or more portions of the second medical data were successfully ingested by the remote server and should be deleted.

In some embodiments, the medical device presents a user interface to the user to display a progress of the data transfer process. For example, the user interface may display a graphical element in the form of a progress bar that is updated as one or more transfer packages in the portion of the first medical data are transferred to the removable data storage device.

In step 310, the medical device updates the transfer status of the portion of the first medical data to the second status after completing the data transfer process. In some embodiments, the user interface presented to the user can be updated to display a message indicating that the data transfer process has completed. Subsequently, the user can disconnect (e.g., unplug) the removable data storage device from the medical device and physically transport and connect the removable data storage device to another computing device capable of accessing the remote server.

In some embodiments, the medical device updates the data-tracking file with an entry that indicates the portion of the first medical data has the second status. In some embodiments, the medical device can be configured to transfer the updated data-tracking file to the removable data storage device. By storing a pre-transfer copy of the data-tracking file before initiating the data transfer and a post-transfer copy of the data-tracking file after completing the data transfer at the removable data storage device, the remote server that later connects to the removable data storage device can determine which portions of data were successfully transferred from the medical device to the removable data storage device. By storing versions of the data-tracking file over multiple data transfer processes, the remote server may better ensure consistency of data transfers over time.

In some embodiments, the medical device can also transfer a copy of a transfer log of the medical device after completion of the data transfer process. As described above with respect to FIG. 1, the transfer log records medical device operations (e.g., user operations or data transfer operations). These logged operations may permit debugging or troubleshooting of faulty data transfers. For example, the transfer log may log instances where transfer fails or user selections.

Figure 4:
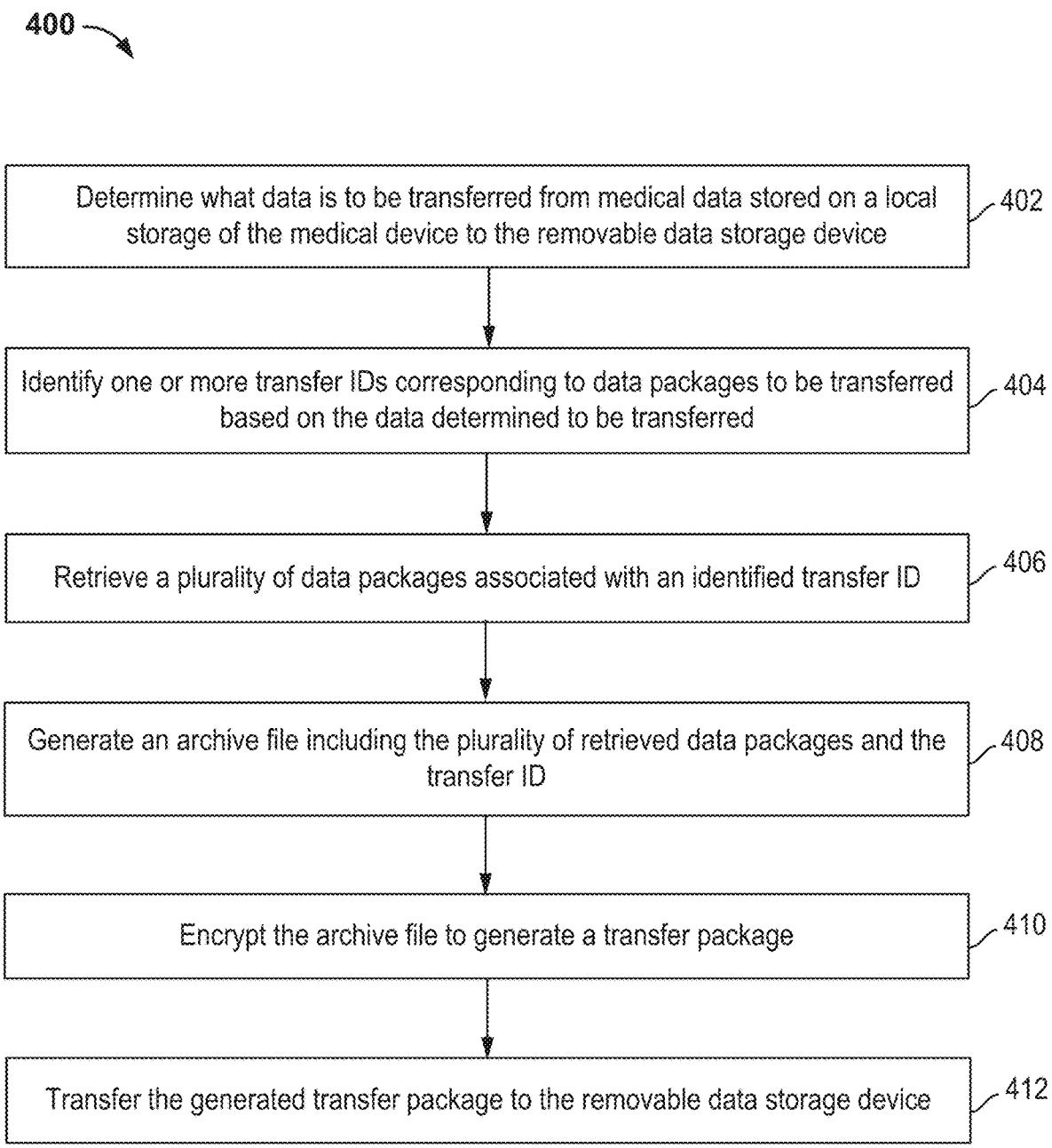
FIG. 4 illustrates a flowchart of a method for generating transfer packages to transfer medical data from a medical device to a removable data storage device, according to some embodiments.

FIG. 4 illustrates a flowchart of a method 400 for generating transfer packages to transfer medical data from a medical device to a removable data storage device, according to some embodiments. In some embodiments, method 400 can be performed by a medical device having a local storage such as medical device 106A of FIG. 1. In some embodiments, method 400 illustrates steps corresponding to steps 306 and 308 as described above with respect to FIG. 3.

In step 402, the medical device determines what data is to be transferred from medical data stored on the local storage to the removable data storage device. In some embodiments, step 402 corresponds to step 306 of FIG. 3. In some embodiments, the medical device can be configured to determine what data to transfer based on reading one or more metadata files from the removable data storage device. For example, the medical device may identify a command file based on the one or more metadata files and retrieve commands that specify which portions of the medical data are to be transferred.

In step 404, the medical device identifies one or more transfer IDs corresponding to data packages to be transferred based on the data determined to be transferred. For example, the medical device may determine that medical data having a first transfer status to be transferred should be transferred. In another example, the medical device may determine that medical data having a transfer ID indicated in the command file should be transferred. In both examples, the medical device may retrieve the one or more transfer IDs that match the determined criteria.

In step 406, the medical device retrieves a plurality of data packages associated with an identified transfer ID. In some embodiments, the medical device determines the plurality of data packages based on a data-tracking file (e.g., data-tracking file 128) that stores associations between transfer IDs and data packages. In some embodiments, the medical data can generate a plurality of source file paths corresponding to the plurality of data packages to permit retrieval of the plurality of data packages.

In step 408, the medical device generates an archive file including the plurality of retrieved data packages and the transfer ID. In some embodiments, the medical device retrieves the plurality of data packages to be combined based on the plurality of corresponding source file paths stored in the data-tracking file. In some embodiments, the medical device can compress the plurality of data packages to generate the archive file. For example, the archive file may be a ZIP file.

In step 410, the medical device encrypts the archive file to generate a transfer package. In some embodiments, the medical device applies an encryption algorithm such as Advanced Encryption Standard (AES) to encrypt the archive file. To apply the encryption algorithm, the medical device may generate and use an encryption key. In some embodiments, the medical device can generate the encryption key based on a user input. For example, the encryption key may be generated based on user credentials, e.g., a password, of the user that initiated the data transfer. In some embodiments, the encryption key can be a predetermined, default key. In other embodiments, the encryption key can be generated based on information specific to the medical device (e.g., device serial number, a file name, a PGP public key, etc.). In some embodiments, the encryption key includes the public key of the remote server such that only the remote server can decrypt the archive file.

In some embodiments, to decrypt the transfer file at a remote server, the remote server would need to generate this same encryption key used to encrypt the archive file. In some embodiments, before a decryption process, the remote server will store a backup copy of the transfer package including the encrypted archive file. If decryption of the transfer package fails, the remote server will be able to restore transfer package using the backup copy of the transfer package.

In some embodiments, the same user that initiated the data transfer from the medical device would also later upload the transferred medical data from the removable data storage device to the remote server. Before allowing the user to upload the medical data, the remote server may first authenticate the user by requesting that the user enter his or her user credentials. Therefore, in these embodiments, the remote server may use the user credentials to generate the same encryption key used to encrypt the transfer package.

In step 412, the medical device transfers the generated transfer package to the removable data storage device. In some embodiments, the medical device can estimate a size of the transfer package based on the plurality of data packages combined in the archive file. For example, the medical device may retrieve the plurality of source file paths of the plurality of corresponding data packages to estimate a size of each data package. In some embodiments, the medical device can determine whether an available storage space on the removable data storage device is greater than the estimated size of the transfer package before initiating transfer of the transfer package.

In some embodiments, the medical device can be configured to perform steps 406-412 for each transfer ID identified in step 404 to transfer a transfer package corresponding to each transfer ID.

In some embodiments, the medical device can be configured to hold a queue of a plurality of generated transfer packages to be transferred to the removable data storage device. In some embodiments, when the medical device generates a transfer package, the medical device can add the transfer package to the queue.

Figure 5:
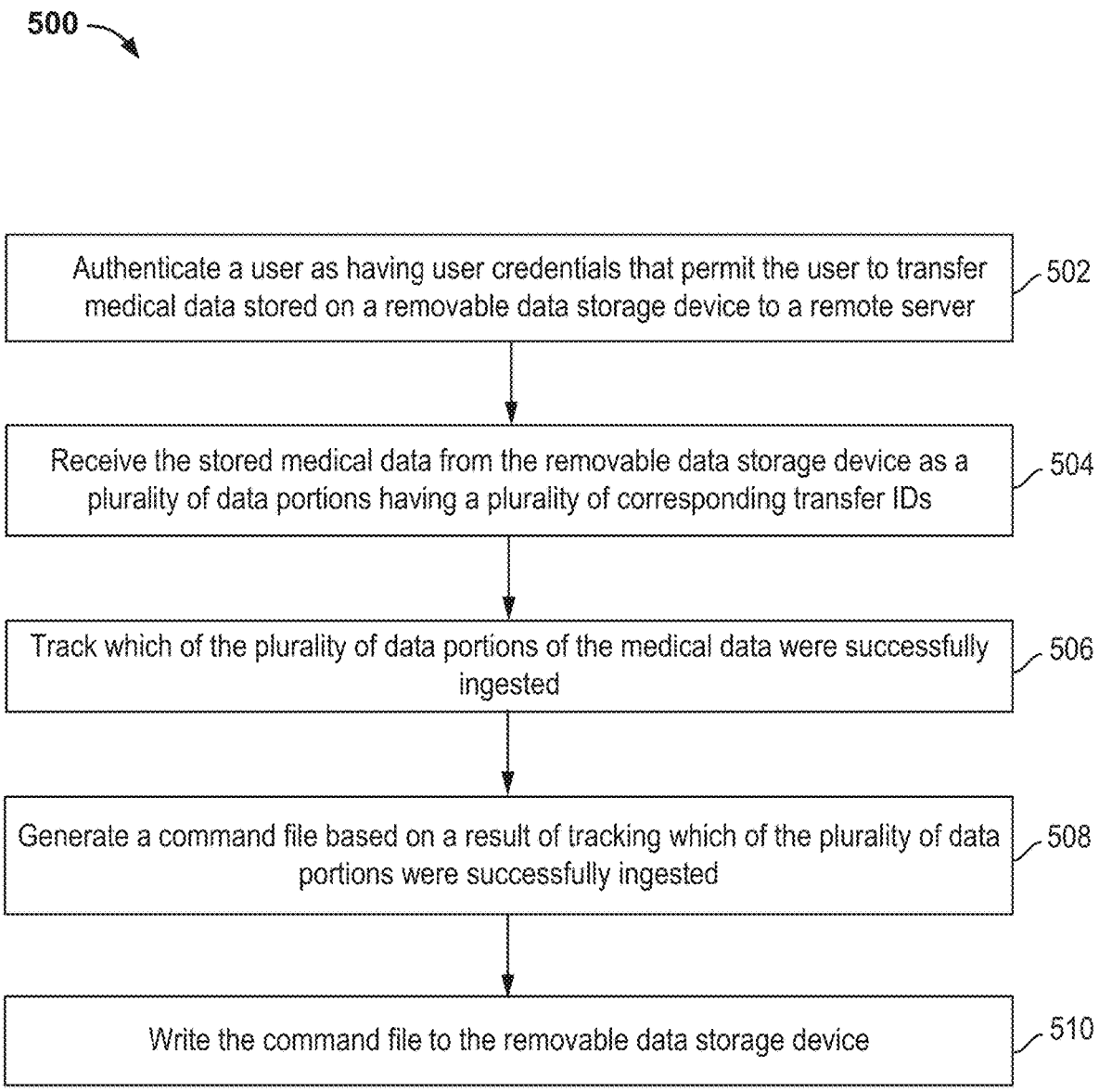
FIG. 5 illustrates a flowchart of a method for transferring medical data from a removable data storage device to a remote server, according to some embodiments.

FIG. 5 illustrates a flowchart of a method 500 for transferring medical data from a removable data storage device to a remote server, according to some embodiments. In some embodiments, method 500 can be performed by a remote server such as remote server 150 of FIG. 1. In some embodiments, the medical data may be stored on a removable data storage device such as removable data storage device 130 of FIG. 1.

In step 502, the remote server authenticates a user as having user credentials that permit the user to transfer medical data stored on the removable data storage device to the remote server. In some embodiments, the remote server can provide a user interface (e.g., a portal or a login screen) that prompts the user to enter his or her user credentials. As shown and described with respect to FIG. 1, the user may access user interface 154 of remote server 150 using a client 142 of a computing device 140.

In some embodiments, the remote server communicatively connects to the removable data storage device storing the medical data. If the remote server does not detect that removable data storage device, the remote server may provide a message in the user interface to request that the user connect the removable data storage device. For example, the user may insert the removable data storage device into a computing device that is communicatively connected to the remote server.

In step 504, the remote server receives the stored medical data from the removable data storage device as a plurality of data portions having a plurality of corresponding transfer IDs. In some embodiments, the medical data is encrypted and the remote server is configured to decrypt the medical data before storing at the remote server. In some embodiments, the remote server can receive one or more data-tracking files stored on the removable data storage device. For example, as described above with respect to FIG. 2, the removable data storage device may receive a pre-transfer version of the data-tracking file and a post-transfer version of the data-tracking file. In some embodiments, the remote server may compare the one or more data-tracking files with each other to validate the data transfer from the medical device to the removable data storage device. If the pre-transfer and post-copy versions of the data-tracking file do not match, the remote server may determine that an error occurred during the data transfer process and may generate a command file to request retransfer of certain portions of medical data, as will be further described below. In some embodiments, the remote server can also receive a transfer log of medical device operations from the removable data storage device.

In step 506, the remote server tracks which of the plurality of data portions of the medical data were successfully ingested. In some embodiments, the remote server tracks which of the plurality of data portions of the medical data were not successfully ingested. For example, the remote server may attempt to ingest the medical data from the removable data storage device to a data storage system operated by the remote server.

In step 508, the remote server generates a command file based on a result of tracking which of the plurality of data portions were successfully ingested. In some embodiments, the command file can include one or more commands that indicate one or more transfer IDs from the removable data storage device whose one or more associated data portions were not successfully ingested and therefore should be retransferred. In some embodiments, the one or more commands can indicate one or more transfer IDs whose one or more associated data portions were successfully ingested. As described above with respect to FIGS. 1-3, this information may be used by a medical device to purge previously-transferred medical data confirmed to be successfully ingested by the remote server. In some embodiments, the one or more commands may include a command to transfer portions of medical data having the first status indicating data to be transferred.

In step 510, the remote server writes the command file to the removable data storage device. In some embodiments, the remote server can be configured to overwrite or delete a previous command file stored on the removable data storage device. In some embodiments, the remote server can be configured to cause the medical data stored on the removable data storage device to be purged (e.g., deleted).

Figure 6:
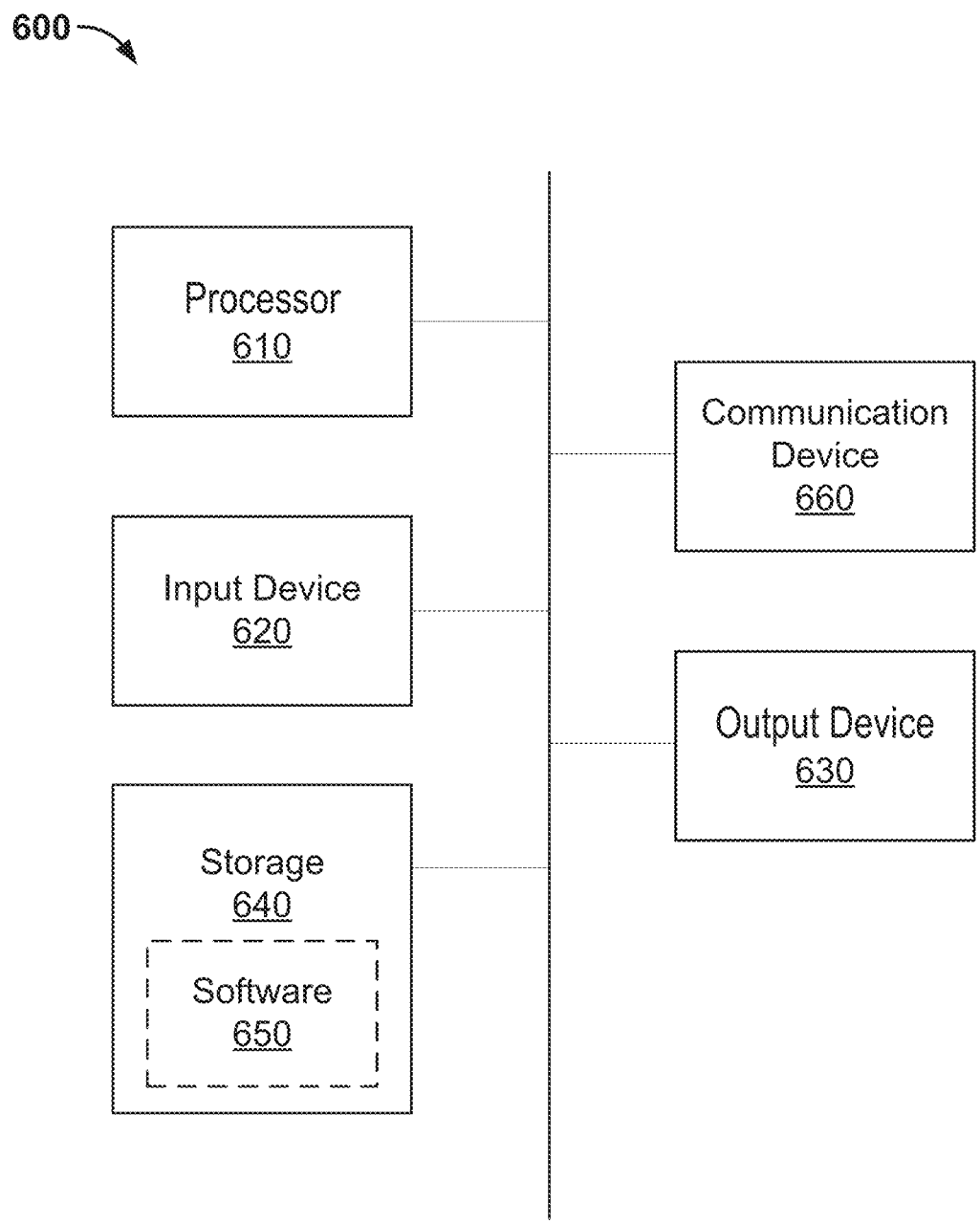
FIG. 6 illustrates an example of a computer, according to some embodiments.

FIG. 6 illustrates an example of a computing device 600, according to some embodiments. Device 600 can be a host computing device connected to a network. For example, device 600 may be an example implementation of one or more of the networked devices, computing device 140, or medical devices 106A-B, described above with respect to FIG. 1. Device 600 can be a client computer or a server. As shown in FIG. 6, device 600 can be any suitable type of microprocessor-based device, such as a personal computer, work station, or server. The device can include, for example, one or more of processor 610, input device 620, output device 630, storage 640, and communication device 660. Input device 620 and output device 630 can generally correspond to those described above and can either be connectable or integrated with the computing device.

Input device 620 can be any suitable device that provides input, such as a touchscreen, keyboard or keypad, mouse, or voice-recognition device. Output device 630 can be any suitable device that provides output, such as a touchscreen, haptics device, or speaker.

Storage 640 can be any suitable device that provides storage, such as an electrical, magnetic, or optical memory including a RAM, cache, hard drive, or removable storage disk. Communication device 660 can include any suitable device capable of transmitting and receiving signals over a network, such as a network interface chip or device. The components of the computing device can be connected in any suitable manner, such as via a physical bus, or wirelessly.

Software 650, which can be stored in storage 640 and executed by processor 610, can include, for example, the programming that embodies the functionality of the present disclosure (e.g., as embodied in the devices described above). For example, software 650 may include system software (e.g., an operating system), application software, or security software.

Software 650 can also be stored and/or transported within any non-transitory, computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 640, that can contain or store programming for use by or in connection with an instruction-execution system, apparatus, or device.

Software 650 can also be propagated within any transport medium for use by or in connection with an instruction-execution system, apparatus, or device, such as those described above, that can fetch instructions associated with the software from the instruction-execution system, apparatus, or device and execute the instructions. In the context of this disclosure, a transport medium can be any medium that can communicate, propagate, or transport programming for use by or in connection with an instruction-execution system, apparatus, or device. The transport readable medium can include, but is not limited to, an electronic, magnetic, optical, electromagnetic, or infrared wired or wireless propagation medium.

Device 600 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 600 can implement any operating system suitable for operating on the network. Software 650 can be written in any suitable programming language, such as C, C++, Java, or Python. In various embodiments, application software embodying the functionality of the present disclosure can be deployed in different configurations, such as in a client/server arrangement, for example.

The foregoing description, for purpose of explanation, has made reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments, with various modifications, that are suited to the particular use contemplated.

Although the disclosure and examples have been fully described with reference to the accompanying figures, it is to be noted that various changes and modifications will be apparent to those skilled in the art. Such changes and modifications are to be understood as being included within the scope of the disclosure and examples as defined by the claims.

What is claimed is:

1. A method for transferring medical data from a medical device to a remote server, comprising:
   at a medical device comprising a local storage:
      tracking a transfer status of medical data stored on the local storage, wherein the stored medical data comprises:
         first medical data having a first status indicating that the first medical data is to be transferred from the local storage on the medical device to the remote server but has not been transferred, and
         second medical data having a second status indicating that the second medical data was previously transferred out of the medical device;
      physically coupling the medical device to a removable data storage device including one or more metadata files;
      determining what data is to be transferred from the medical device to the removable data storage device based on the one or more metadata files;
      initiating a data transfer process to transfer at least a portion of the first medical data to the removable data storage device based on information determined from reading the one or more metadata files; and
      after completing the data transfer process, updating the transfer status of the portion of the first medical data to the second status.

2. The method of claim 1, wherein the stored medical data is obtained in association with a patient, the stored medical data comprising one or more of a sensor reading of a vital sign of the patient, an image of a portion of the patient, a video of a medical procedure of the patient, demographic information of the patient, or information entered by a medical practitioner.

3. The method of claim 1, wherein the medical device is configured to be operated in a hospital and configured to be disconnected from all networks external to the hospital.

4. The method of claim 1, comprising:
   receiving third medical data at the medical device;
   determining that the third medical data is prohibited from being transferred out of the medical device; and
   storing the third medical data to the local storage without associating any transfer statuses with the stored third medical data.

5. The method of claim 4, wherein the third medical data comprises personally identifiable information (PII).

6. The method of claim 1, comprising:
   determining an available storage space on the removable data storage device based on reading the one or more metadata files, wherein the portion of the first medical data is transferred to the removable data storage device based on the determined available storage space.

7. The method of claim 1, comprising:
   determining whether the removable data storage device has a command file for controlling what data the medical device is to transfer based on reading the one or more metadata files; and wherein the data transfer process is initiated to transfer the portion of the first medical data to the removable data storage device in response to determining that the removable data storage device does not have the command file.

8. The method of claim 1, comprising:
identifying a command file stored on the removable data storage device based on reading the one or more metadata files, wherein the command file includes information that controls what data is to be transferred from the medical device to the removable data storage device; and
wherein the data transfer process is initiated to transfer the portion of the first medical data to the removable data storage device based on the information in the command file.

9. The method of claim 8, wherein the information in the command file comprises a command to transfer any data having the first status from the medical device to the removable data storage device.

10. The method of claim 8, wherein the information in the command file comprises a command to retransfer previously-transferred data from the medical device to the removable data storage device, and wherein the data transfer process comprises:
transferring the second medical data having the second status to the removable data storage device based on the command to retransfer previously-transferred data.

11. The method of claim 8, wherein the information in the command file comprises one or more commands that specify one or more transfer identifiers (IDs) whose corresponding data is to be transferred from the medical device to the removable data storage device, and wherein the data transfer process comprises:
identifying one or more portions of the second medical data corresponding to the one or more transfer IDs in the one or more commands; and
transferring the one or more identified portions of the second medical data to the removable data storage device.

12. The method of claim 8, wherein the information in the command file indicates which portions of the second medical data were successfully ingested by the remote server.

13. The method of claim 12, wherein the information in the command file comprises second transfer IDs corresponding to the portions of the second medical data.

14. The method of claim 12, comprising:
assigning a third status to the portions of the second medical data indicated in the information in the command file, wherein any medical data assigned the third status indicates that the medical data has been successfully ingested by the remote server and is to be purged from the medical device.

15. The method of claim 1, wherein the stored medical data comprises a plurality of data packages assigned a plurality of corresponding transfer identifiers (IDs).

16. The method of claim 15, wherein a first transfer ID for a first data package comprises information indicating a patient, an encounter with the patient that generated the data package, or a data sequence, wherein the information indicating the patient enables the remote server to associate other data packages having the same information indicating the patient with the first data package.

17. The method of claim 1, wherein the portion of the first medical data comprises a plurality of data packages associated with a plurality of transfer IDs, and wherein initiating the data transfer process comprises:
retrieving the transfer IDs to generate a list of the plurality of data packages to be transferred based on reading the one or more metadata files;
creating a first transfer package for a first transfer ID of the retrieved transfer IDs, wherein the first transfer package comprises first data packages associated with the first transfer ID; and
encrypting the first transfer package before transferring the encrypted first transfer package to the removable data storage device.

18. The method of claim 17, wherein creating the transfer package comprises:
identifying first source file paths for the first data packages based on the first transfer ID; and
combining data from the first data packages based on the identified first source file paths to create an archive file.

19. The method of claim 1, wherein updating the transfer status of the portion of the first medical data comprises:
adding to a transfer log one or more entries comprising information that assigns the portion of the first user data with the second status.

20. The method of claim 1, wherein the medical data stored on the local storage comprises medical data generated in response to a user interacting with the medical device.

21. The method of claim 20, comprising
determining which portions of the generated medical data are to be transferred to the remote server based on data types or data sources of the respective portions; and
updating a transfer log to indicate that the portions of the generated medical data determined to be transferred have the first status.

22. The method of claim 20, comprising:
providing a graphical user interface (GUI) to enable the user to interact with the medical device; and
determining whether a portion of the generated medical data is to be transferred based on how the user interacts with the GUI.

23. The method of claim 22, wherein the GUI provides a plurality of graphical elements, and wherein whether the portion of the generated medical data is to be transferred is determined based on which graphical element the user interacted with to generate the portion.

24. The method of claim 1, comprising:
updating a data-tracking file during the data transfer process, the data-tracking file comprising information that specifies what data was successfully transferred from the medical device to the removable data storage device; and
after completing the data transfer process, transmitting the updated data-tracking file to the removable data storage device.

25. The method of claim 24, comprising:
transmitting a copy of the data-tracking file to the removable data storage device before initiating the data transfer process.

26. The method of claim 1, comprising:
presenting to a user operating the removable data storage device a user interface that requests the user to enter a user credential; and
in response to authenticating the user credential, presenting a graphical element on a screen of the medical device to enable the user to initiate the data transfer process,
wherein the data transfer process is initiated in response to receiving the user's selection of the graphical element.

27. The method of claim 1, wherein the medical device receives a request from the remote server for information identifying medical data stored on the local storage, and transmits the requested information to the remote server for the remote server to use to generate the command file.

28. The method of claim 27, wherein the requested information comprises metadata identifying at least the first medical data.

29. The method of claim 1, wherein the first medical data is encrypted with a public key of the remote server.

30. A system for transferring medical data from a medical device to a remote server, comprising:
   one or more processors;
   memory comprising a local storage; and
   one or more programs, wherein the one or more programs are stored in the memory and configured to be executed by the one or more processors, the one or more programs including instructions for:
   tracking a transfer status of medical data stored on the local storage, wherein the stored medical data comprises:
      first medical data having a first status indicating that the first medical data is to be transferred from the local storage on the medical device to the remote server but has not been transferred, and
      second medical data having a second status indicating that the second medical data was previously transferred out of the medical device;
   physically coupling the medical device to a removable data storage device including one or more metadata files;
   determining what data is to be transferred from the medical device to the removable data storage device based on the one or more metadata files;
   initiating a data transfer process to transfer at least a portion of the first medical data to the removable data storage device based on information determined from reading the one or more metadata files; and
   after completing the data transfer process, updating the transfer status of the portion of the first medical data to the second status.

31. A non-transitory computer-readable storage medium comprising one or more programs for transferring medical data from a medical device to a remote server, wherein the one or more programs, when executed by one or more processors, cause the one or more processors to perform operations comprising:
   tracking a transfer status of medical data stored on the local storage, wherein the stored medical data comprises:
      first medical data having a first status indicating that the first medical data is to be transferred from the local storage on the medical device to the remote server but has not been transferred, and
      second medical data having a second status indicating that the second medical data was previously transferred out of the medical device;
   physically coupling the medical device to a removable data storage device including one or more metadata files;
   determining what data is to be transferred from the medical device to the removable data storage device based on the one or more metadata files;
   initiating a data transfer process to transfer at least a portion of the first medical data to the removable data storage device based on information determined from reading the one or more metadata files; and
   after completing the data transfer process, updating the transfer status of the portion of the first medical data to the second status.

32. The system of claim 30, wherein the stored medical data is obtained in association with a patient, the stored medical data comprising one or more of a sensor reading of a vital sign of the patient, an image of a portion of the patient, a video of a medical procedure of the patient, demographic information of the patient, or information entered by a medical practitioner.

33. The system of claim 30, wherein the medical device is configured to be operated in a hospital and configured to be disconnected from all networks external to the hospital.

34. The system of claim 30, wherein the one or more programs include instructions for:
   receiving third medical data at the medical device;
   determining that the third medical data is prohibited from being transferred out of the medical device; and
   storing the third medical data to the local storage without associating any transfer statuses with the stored third medical data.

35. The system of claim 34, wherein the third medical data comprises personally identifiable information (PII).

36. The system of claim 30, wherein the one or more programs include instructions for:
   determining an available storage space on the removable data storage device based on reading the one or more metadata files, wherein the portion of the first medical data is transferred to the removable data storage device based on the determined available storage space.

37. The system of claim 30, wherein the one or more programs include instructions for:
   determining whether the removable data storage device has a command file for controlling what data the medical device is to transfer based on reading the one or more metadata files, wherein the data transfer process is initiated to transfer the portion of the first medical data to the removable data storage device in response to determining that the removable data storage device does not have the command file.

38. The system of claim 30, wherein the one or more programs include instructions for:
   identifying a command file stored on the removable data storage device based on reading the one or more metadata files, wherein the command file includes information that controls what data is to be transferred from the medical device to the removable data storage device, wherein the data transfer process is initiated to transfer the portion of the first medical data to the removable data storage device based on the information in the command file.

39. The system of claim 38, wherein the information in the command file comprises a command to transfer any data having the first status from the medical device to the removable data storage device.

40. The system of claim 38, wherein the information in the command file comprises a command to retransfer previously-transferred data from the medical device to the removable data storage device, and wherein the data transfer process comprises:
   transferring the second medical data having the second status to the removable data storage device based on the command to retransfer previously-transferred data.

41. The system of claim 38, wherein the information in the command file comprises one or more commands that specify one or more transfer identifiers (IDs) whose corresponding data is to be transferred from the medical device to the removable data storage device, and wherein the data transfer process comprises:
  identifying one or more portions of the second medical data corresponding to the one or more transfer IDs in the one or more commands; and
  transferring the one or more identified portions of the second medical data to the removable data storage device.

42. The system of claim 38, wherein the information in the command file indicates which portions of the second medical data were successfully ingested by the remote server.

43. The system of claim 42, wherein the information in the command file comprises second transfer IDs corresponding to the portions of the second medical data.

44. The system of claim 42, wherein the one or more programs include instructions for assigning a third status to the portions of the second medical data indicated in the information in the command file, wherein any medical data assigned the third status indicates that the medical data has been successfully ingested by the remote server and is to be purged from the medical device.

45. The system of claim 30, wherein the stored medical data comprises a plurality of data packages assigned a plurality of corresponding transfer identifiers (IDs).

46. The system of claim 45, wherein a first transfer ID for a first data package comprises information indicating a patient, an encounter with the patient that generated the data package, or a data sequence, wherein the information indicating the patient enables the remote server to associate other data packages having the same information indicating the patient with the first data package.

47. The system of claim 30, wherein the portion of the first medical data comprises a plurality of data packages associated with a plurality of transfer IDs, and wherein initiating the data transfer process comprises:
  retrieving the transfer IDs to generate a list of the plurality of data packages to be transferred based on reading the one or more metadata files;
  creating a first transfer package for a first transfer ID of the retrieved transfer IDs, wherein the first transfer package comprises first data packages associated with the first transfer ID; and
  encrypting the first transfer package before transferring the encrypted first transfer package to the removable data storage device.

48. The system of claim 47, wherein creating the transfer package comprises:
  identifying first source file paths for the first data packages based on the first transfer ID; and
  combining data from the first data packages based on the identified first source file paths to create an archive file.

49. The system of claim 30, wherein updating the transfer status of the portion of the first medical data comprises adding to a transfer log one or more entries comprising information that assigns the portion of the first user data with the second status.

50. The system of claim 30, wherein the medical data stored on the local storage comprises medical data generated in response to a user interacting with the medical device.

51. The system of claim 50, wherein the one or more programs include instructions for:
  determining which portions of the generated medical data are to be transferred to the remote server based on data types or data sources of the respective portions; and
  updating a transfer log to indicate that the portions of the generated medical data determined to be transferred have the first status.

52. The system of claim 50, wherein the one or more programs include instructions for:
  providing a graphical user interface (GUI) to enable the user to interact with the medical device; and
  determining whether a portion of the generated medical data is to be transferred based on how the user interacts with the GUI.

53. The system of claim 52, wherein the GUI provides a plurality of graphical elements, and wherein whether the portion of the generated medical data is to be transferred is determined based on which graphical element the user interacted with to generate the portion.

54. The system of claim 30, wherein the one or more programs include instructions for:
  updating a data-tracking file during the data transfer process, the data-tracking file comprising information that specifies what data was successfully transferred from the medical device to the removable data storage device; and
  after completing the data transfer process, transmitting the updated data-tracking file to the removable data storage device.

55. The system of claim 54, wherein the one or more programs include instructions for transmitting a copy of the data-tracking file to the removable data storage device before initiating the data transfer process.

56. The system of claim 30, wherein the one or more programs include instructions for:
  presenting to a user operating the removable data storage device a user interface that requests the user to enter a user credential; and
  in response to authenticating the user credential, presenting a graphical element on a screen of the medical device to enable the user to initiate the data transfer process,
  wherein the data transfer process is initiated in response to receiving the user's selection of the graphical element.

57. The system of claim 30, wherein the medical device receives a request from the remote server for information identifying medical data stored on the local storage, and transmits the requested information to the remote server for the remote server to use to generate the command file.

58. The system of claim 57, wherein the requested information comprises metadata identifying at least the first medical data.

59. The system of claim 30, wherein the first medical data is encrypted with a public key of the remote server.

* * * * *